(12) United States Patent
Wenger et al.

(10) Patent No.: US 10,342,587 B2
(45) Date of Patent: Jul. 9, 2019

(54) MEDICAL DEVICE, APPARATUS, AND SURGICAL METHOD

(71) Applicant: SpineWelding AG, Schlieren (CH)

(72) Inventors: Andreas Wenger, Muri b. Bern (CH); Jörg Mayer, Niederlenz (CH)

(73) Assignee: SPINEWELDING AG, Schlieren (CH)

( * ) Notice: Subject to any disclaimer, the term of this patent is extended or adjusted under 35 U.S.C. 154(b) by 0 days.

(21) Appl. No.: 15/404,268

(22) Filed: Jan. 12, 2017

(65) Prior Publication Data

US 2017/0119447 A1 May 4, 2017

Related U.S. Application Data

(60) Division of application No. 14/838,772, filed on Aug. 28, 2015, now Pat. No. 9,566,099, which is a
(Continued)

(51) Int. Cl.
| | | |
|---|---|---|
| A61B 17/70 | (2006.01) | |
| A61B 17/88 | (2006.01) | |
| A61B 17/68 | (2006.01) | |
| A61B 17/86 | (2006.01) | |
| A61C 8/00 | (2006.01) | |

(Continued)

(52) U.S. Cl.
CPC .... *A61B 17/8811* (2013.01); *A61B 17/00491* (2013.01); *A61B 17/68* (2013.01); *A61B 17/686* (2013.01); *A61B 17/7001* (2013.01); *A61B 17/7032* (2013.01); *A61B 17/7098* (2013.01); *A61B 17/863* (2013.01); *A61B 17/864* (2013.01); *A61B 17/8822* (2013.01); *A61B 17/8894* (2013.01); *A61C 8/0012* (2013.01); *A61C 8/0033* (2013.01); *A61F 2/2846* (2013.01); *A61B 17/320068* (2013.01); *A61B 17/866* (2013.01); *A61B 2017/8655* (2013.01);
(Continued)

(58) Field of Classification Search
CPC .......... A61B 17/7032–17/7046; A61B 17/864
See application file for complete search history.

(56) References Cited

U.S. PATENT DOCUMENTS

| 3,025,853 | A | | 3/1962 | Mason | |
|---|---|---|---|---|---|
| 4,653,489 | A | * | 3/1987 | Tronzo | ................. A61B 17/746 606/304 |

(Continued)

FOREIGN PATENT DOCUMENTS

| CN | 2577785 | 10/2003 |
|---|---|---|
| EP | 2596764 | 5/2013 |

(Continued)

*Primary Examiner* — Eduardo C Robert
*Assistant Examiner* — Michelle C Eckman
(74) *Attorney, Agent, or Firm* — Rankin, Hill & Clark LLP

(57) ABSTRACT

A pedicle anchor device is equipped for being used like a pedicle screw, i.e. for being implanted in the vertebra from dorsal direction (but generally at an angle to the sagittal plane, slightly inward towards the sagittal plane) through the pedicle so that a distal portion of the device protrudes into the vertebral body. The pedicle anchor device includes a pedicle anchor device body with a head portion, a shaft portion and a longitudinal bore that extends from a proximal end of the pedicle anchor device body and has a hole or a plurality of holes from the longitudinal bore outward, for example radially outward.

13 Claims, 6 Drawing Sheets

Related U.S. Application Data continuation of application No. 13/503,950, filed as application No. PCT/CH2010/000280 on Nov. 9, 2010, now Pat. No. 9,155,563.

(60) Provisional application No. 61/259,383, filed on Nov. 9, 2009, provisional application No. 61/388,243, filed on Sep. 30, 2010, provisional application No. 61/394,580, filed on Oct. 19, 2010.

(51) Int. Cl.
| | | |
|---|---|---|
| *A61B 17/00* | (2006.01) | |
| *A61F 2/28* | (2006.01) | |
| A61B 17/32 | (2006.01) | |
| A61C 19/06 | (2006.01) | |

(52) U.S. Cl.
CPC ....... *A61C 19/063* (2013.01); *A61F 2002/285* (2013.01)

(56) References Cited

U.S. PATENT DOCUMENTS

| | | | |
|---|---|---|---|
| 5,300,074 A | 4/1994 | Frigg | |
| 6,048,343 A * | 4/2000 | Mathis | A61B 17/7098 606/304 |
| 6,409,730 B1 | 6/2002 | Green et al. | |
| 6,436,100 B1 * | 8/2002 | Berger | A61B 17/60 411/394 |
| 6,554,830 B1 * | 4/2003 | Chappius | A61B 17/3472 606/246 |
| 6,730,095 B2 | 5/2004 | Olson et al. | |
| 6,921,264 B2 | 7/2005 | Mayer et al. | |
| 7,335,205 B2 | 2/2008 | Aeschlimann et al. | |
| 7,717,947 B1 | 5/2010 | Wilberg et al. | |
| 7,837,709 B2 | 11/2010 | Dutoit et al. | |
| 8,092,505 B2 * | 1/2012 | Sommers | A61B 17/68 606/317 |
| 8,579,948 B2 | 11/2013 | Biedermann et al. | |
| 8,617,226 B2 | 12/2013 | Kim | |
| 8,740,954 B2 | 6/2014 | Ghobrial et al. | |
| 8,808,337 B2 * | 8/2014 | Sweeney | A61B 17/7061 604/264 |
| 8,834,542 B2 * | 9/2014 | Mayer | A61B 17/0401 606/310 |
| 9,173,692 B1 * | 11/2015 | Kaloostian | A61B 17/8685 |
| 9,788,865 B2 * | 10/2017 | Matthis | A61B 17/7037 |
| 9,936,992 B2 * | 4/2018 | Russell | A61B 17/864 |
| 9,943,350 B2 * | 4/2018 | Wenger | A61B 17/8811 |
| 2001/0021852 A1 * | 9/2001 | Chappius | A61B 17/3472 600/300 |
| 2004/0015172 A1 * | 1/2004 | Biedermann | A61B 17/864 606/304 |
| 2004/0053196 A1 | 3/2004 | Mayer et al. | |
| 2004/0068258 A1 * | 4/2004 | Schlapfer | A61B 17/70 606/261 |
| 2004/0122431 A1 * | 6/2004 | Biedermann | A61B 17/864 606/62 |
| 2004/0147929 A1 * | 7/2004 | Biedermann | A61B 17/7001 606/266 |
| 2004/0225292 A1 * | 11/2004 | Sasso | A61B 17/8615 606/916 |
| 2004/0230195 A1 * | 11/2004 | Kaikkonen | A61B 17/863 606/316 |
| 2004/0267265 A1 * | 12/2004 | Kyle | A61B 17/7098 606/304 |
| 2005/0015059 A1 * | 1/2005 | Sweeney | A61B 17/864 604/264 |
| 2005/0015060 A1 * | 1/2005 | Sweeney | A61B 17/864 604/264 |
| 2005/0107800 A1 * | 5/2005 | Frankel | A61B 17/1655 606/92 |
| 2006/0271053 A1 | 11/2006 | Schlapfer et al. | |
| 2007/0161985 A1 | 7/2007 | Demakas et al. | |
| 2007/0260250 A1 * | 11/2007 | Wisnewski | A61B 17/7098 606/262 |
| 2007/0270858 A1 * | 11/2007 | Trieu | A61B 17/7098 606/279 |
| 2007/0299450 A1 * | 12/2007 | Her | A61B 17/7032 606/279 |
| 2008/0045962 A1 | 2/2008 | Aeschlimann et al. | |
| 2008/0125815 A1 | 5/2008 | Heaven et al. | |
| 2008/0132956 A1 * | 6/2008 | Biedermann | A61B 17/7032 606/300 |
| 2008/0132957 A1 * | 6/2008 | Matthis | A61B 17/7032 606/301 |
| 2008/0249574 A1 * | 10/2008 | McCombs | A61B 17/8625 606/301 |
| 2008/0262517 A1 * | 10/2008 | Wieland | A61B 17/00491 606/151 |
| 2009/0018560 A1 * | 1/2009 | Mayer | A61F 2/30721 606/151 |
| 2009/0018590 A1 * | 1/2009 | Dorawa | A61B 17/864 606/301 |
| 2010/0004692 A1 * | 1/2010 | Biedermann | A61B 17/7037 606/305 |
| 2010/0042167 A1 * | 2/2010 | Nebosky | A61B 17/7061 606/315 |
| 2010/0042215 A1 * | 2/2010 | Stalcup | A61B 17/68 623/16.11 |
| 2010/0106199 A1 * | 4/2010 | Sawa | A61B 17/7098 606/304 |
| 2010/0114174 A1 * | 5/2010 | Jones | A61B 17/7098 606/279 |
| 2011/0004256 A1 * | 1/2011 | Biedermann | A61B 17/7098 606/301 |
| 2011/0060373 A1 * | 3/2011 | Russell | A61B 17/0401 606/304 |
| 2011/0196425 A1 * | 8/2011 | Rezach | A61B 17/7035 606/278 |
| 2011/0245881 A1 * | 10/2011 | Mitchell | A61B 17/7098 606/304 |
| 2011/0282418 A1 * | 11/2011 | Saunders | A61B 17/7002 607/105 |
| 2011/0288599 A1 * | 11/2011 | Michielli | A61B 17/7037 606/305 |
| 2012/0029432 A1 * | 2/2012 | Sweeney | A61B 17/3472 604/151 |
| 2012/0029578 A1 * | 2/2012 | Suh | A61B 17/7035 606/309 |
| 2012/0041395 A1 * | 2/2012 | Sweeney | A61B 17/7061 604/272 |
| 2012/0089195 A1 * | 4/2012 | Yedlicka | A61B 17/8635 606/304 |
| 2012/0123485 A1 * | 5/2012 | Dehnad | A61K 33/30 606/304 |
| 2012/0226318 A1 * | 9/2012 | Wenger | A61B 17/7032 606/264 |
| 2013/0184761 A1 | 7/2013 | Biedermann et al. | |
| 2013/0211466 A1 * | 8/2013 | Ballard | A61B 17/8635 606/323 |
| 2014/0046379 A1 * | 2/2014 | Sweeney | A61B 17/864 606/304 |
| 2014/0094860 A1 * | 4/2014 | Reimels | A61B 17/844 606/323 |
| 2014/0236242 A1 * | 8/2014 | Robinson | A61B 17/8605 606/279 |
| 2015/0057711 A1 * | 2/2015 | Kim | A61B 17/7032 606/304 |
| 2016/0374740 A1 * | 12/2016 | Donald | A61B 17/864 606/304 |
| 2017/0119444 A1 * | 5/2017 | Reed | A61B 17/863 |
| 2017/0231671 A1 * | 8/2017 | Wilke | A61B 17/7097 606/104 |

FOREIGN PATENT DOCUMENTS

| | | |
|---|---|---|
| JP | 7051292 | 2/1995 |
| JP | 2003-532459 | 11/2003 |

(56) References Cited

FOREIGN PATENT DOCUMENTS

| | | |
|---|---|---|
| JP | 2005-536255 | 12/2005 |
| SU | 1337074 | 9/1987 |
| WO | 90/02526 | 3/1990 |
| WO | 98/51241 | 11/1998 |
| WO | 20080058403 | 5/2008 |
| WO | 2009/010234 | 1/2009 |
| WO | 2009010247 | 1/2009 |
| WO | 2009/055952 | 5/2009 |
| WO | 2009/0117837 | 10/2009 |
| WO | 2009/131955 | 10/2009 |
| WO | 2009/132472 | 11/2009 |

* cited by examiner

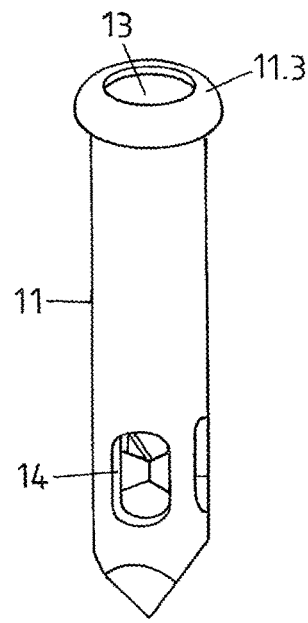 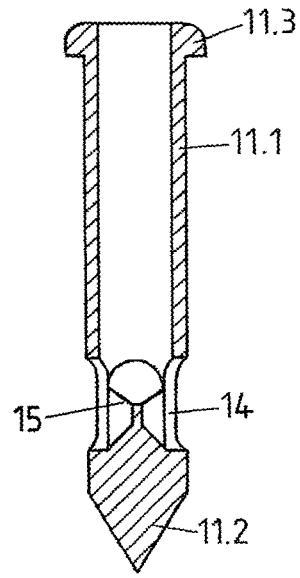 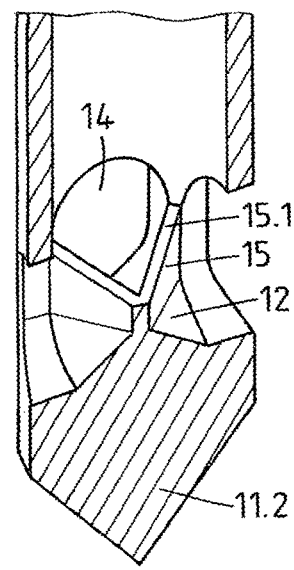
Fig. 15    Fig. 16    Fig. 17
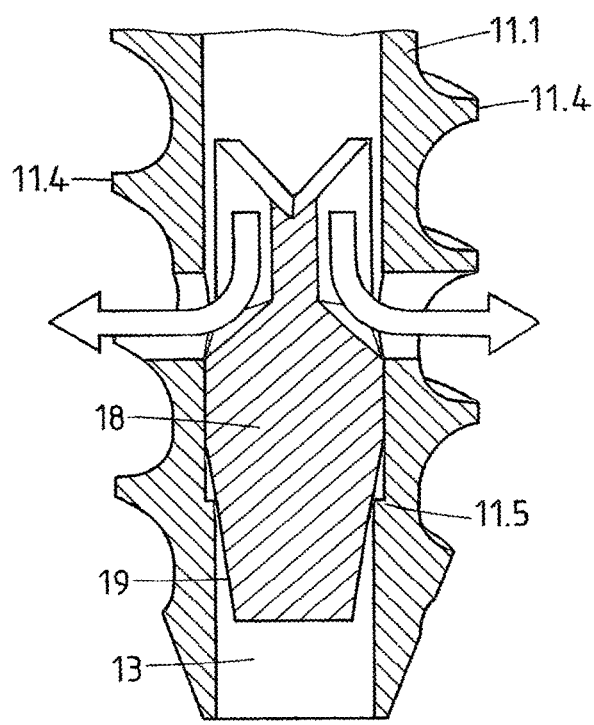 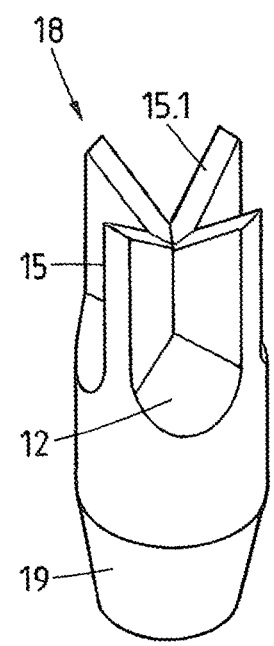
Fig. 18    Fig. 19

MEDICAL DEVICE, APPARATUS, AND SURGICAL METHOD

FIELD OF THE INVENTION

The invention is in the field of medical technology. In particular, it relates to medical devices, medical apparatus and medical methods, especially to implants, apparatuses for implantation, and implantation methods.

BACKGROUND OF THE INVENTION

If screws are anchored in live bone tissue of the vertebrae, often the problem of insufficient bone stability or insufficient stability of the anchoring in the bone arises. Especially, in trabecular bone tissue, any load acting on the screw is passed over to only few trabeculae, with adverse consequences both for the load bearing capability of the screw-bone connection and for its long-time stability. This is especially severe in osteoporotic or osteopenic or otherwise weakened vertebral bone tissue.

An important group of screws anchored in the vertebral bone tissue are pedicle screws. Pedicle screws comprise a screw head for being affixed to a rod or other spine stabilizing device and a threaded screw shaft to be implanted in the vertebra from a dorsal direction through the pedicle so that it protrudes into the vertebral body. Pedicle screws are thus part of a stabilization arrangement of the vertebral column, and they therefore are subject to substantial mechanical loads.

SUMMARY OF THE INVENTION

It is an object of the present invention to provide a medical device and a method that overcome drawbacks of existing pedicle screws and an according spine stabilization method.

In accordance with a first aspect of the invention, a pedicle anchor device is provided. The pedicle anchor device is equipped for being used like a pedicle screw, i.e. for being implanted in the vertebra from dorsal direction (but generally at an angle to the sagittal plane, slightly inward towards the sagittal plane) through the pedicle so that a distal portion of the device protrudes into the vertebral body. The pedicle anchor device comprises a pedicle anchor device body. A proximal portion of the pedicle anchor device body has a head portion that serves for securing an orthopaedic rod or other device that stabilizes the spinal column. The pedicle anchor device body thus has a head portion and a shaft portion. The head portion and the shaft portion may be of one piece, or the head portion may be connected to the shaft portion by a multi-axial or other connection. The shaft portion is capable of being anchored, like a pedicle screw shaft (sometimes referred to as 'stem'), in the vertebra. The head portion may for example be formed like head portions of any prior art pedicle screws, or may be formed in accordance with the specifications of a new spine stabilizing system. The main requirement of the head portion is that it serves for either directly being affixed to a rod or other spine stabilizing device or for being affixed to an intermediate device to which a rod (or other spine stabilizing device and/or other intermediate device) can be affixed.

The pedicle anchor device body according to the first aspect of the invention further has a longitudinal bore that extends from a proximal end of the pedicle anchor device body and has a hole or a plurality of holes from the longitudinal bore outward, for example radially outward.

Further, the pedicle anchor device comprises a liquefiable element that is insertable or inserted in the longitudinal bore and at least partly liquefiable by the impact of energy impinging from the proximal side so that liquefied material flows through the holes in the wall and out of the longitudinal bore into structures of the hard tissue and/or hard tissue replacement material. Thereby, after solidification of the liquefiable (preferably thermoplastic) material, the an anchoring of the positive-fit connection kind is achieved in the hard tissue/hard tissue replacement material.

The liquefiable element may be a single, one-piece element. Such a single one-piece element may be advantageous in terms of transmitting mechanical energy from a proximal to a distal end. Alternatively, a plurality of liquefiable elements may be present, such as a plurality of shaped pieces, chips, flakes, etc.

The principle liquefying, by the impact of mechanical energy, material in a sleeve element (in this text, we refer to sleeve element or tube element or sheath element generally to mean an element with a longitudinal bore with openings ranging from the bore to an outside, without restriction to a particular outer shape) with lateral openings and of pressing liquefied material out of the sleeve element with lateral openings is for example described in U.S. Pat. Nos. 7,335, 205, 6,921,264, WO 2009/055 952, WO 2009/010247, WO 2009/010234, and PCT application No. PCT/CH 2009/ 000138, all of which are incorporated herein by reference.

In a first group of embodiments, the pedicle anchor device is a pedicle screw, wherein the shaft is threaded.

In some embodiments of the first group of embodiments, the thread has a constant outer diameter (major diameter), whereas a core diameter (minor diameter) is larger at the proximal side than at the distal side. For example, the core diameter may be gradually reduced along the entire length of the threaded section, or the core diameter has a stepped characteristics, or has any other characteristics. In other, alternative embodiments, the core diameter is constant.

In the embodiments of the first group of embodiments, anchoring is achieved by a combination of the effect of the thread and the effect of the liquefiable, re-solidified material interpenetrating structures of the hard tissue/hard tissue replacement material.

In accordance with a second group of embodiments, the shaft of the pedicle anchor device is not threaded.

In these embodiments, the shaft may have a non-circular cross section. For example, the shaft may be flattish so as to be blade-like. Especially, the shaft may be such as to have, where it penetrates the pedicle, a larger longitudinal than transversal extension such as to follow the pedicle's shape. In an example, the shaft may be at an acute angle to the transverse plane so that the larger extension perpendicular to the proximodistal axis is in the direction approximately corresponding to the corresponds direction of the larger extension of the pedicle (in section perpendicular to the proximodistal axis).

A non-circular cross section may in addition if necessary provide additional stability against twisting movements.

In special embodiments, the shaft may have a non-circular cross section and may be twisted. Such a twist brings about an improved effective anchoring cross section: larger and other portions of the tissue may contribute to the anchoring.

If the shaft is twisted, generally non-zero twists up to 270° are preferred, since up to about 270° the orientation within the pedicle may approximately use the space available within the pedicle, whereas much stronger twists would lead to the anchor device being substantially twisted within the pedicle so that the dimension of largest extension of the shaft would have to be adapted to the smaller cross sectional extension of the pedicle (in cross section perpendicular to an implantation axis). More in general, a preferred range for the twist of the pedicle anchor device over its entire length may be between 10° and 270°.

For example, the shaft may be twisted into about a quarter of a helix, especially by about 80°-120°, so that a blade plane at the distal end is approximately perpendicular to a blade plane at the proximal end of the shaft. For example, a rod receiving head portion (or other means for affixing a spinal column stabilizer) may be oriented relative to the twisted shaft so that the blade plane at the proximal end of the shaft is oriented approximately parallel to a longitudinal direction and at the distal end of the shaft is oriented approximately parallel to a transversal direction (these terms of direction are to be understood to apply locally, referring to a spine axis). By this special configuration, it is possible to provide a comparably large cross section shaft that anchors well without the relatively small transversal extension of some pedicles without overly limiting the cross section of the shaft. In addition, the pedicle anchor device may extend transversally in the vertebral body so as to provide superior stability especially against angular momenta acting on the anchor that cause longitudinal (up and down) forces on the distal end of the anchor and that often arise during body movements of the patient.

In embodiments of the second group of embodiments where the shaft does not have a circular cross section, the shaft may be slightly tapered to add a press fit effect to the anchoring effects achieved by the mere shape and by the liquefied and re-solidified material.

In embodiments of the second group of embodiments where the shaft does not have a circular cross section but is flattish, the holes from the longitudinal bore outward may especially include openings on each of the two flat sides. Additional holes on at least one of the small sides and/or at the distal end may be present. An additional, axial hole at the distal end may be advantageous during surgery because it allows guidance of the anchor during insertion by means of a K wire or similar device. Such an axial hole may be arranged in the center (with respect to the axis) or off-center. Depending on the parameters 'hole diameter' and 'hole depth', (also in relation to the according parameters of the other hole(s) along the circumference), the axial hole may be such that liquefied material is pressed out through the hole into the tissue, or that the liquefied material that gets into the axial hole freezes before it reaches the hole exit so that a plug of the liquefiable, re-solidified material is created.

The invention also concerns a method of implanting a pedicle anchor device according to the second aspect by a method having at least one method step of the method described referring to the figures. Especially, a method of anchoring a pedicle anchor device may comprise the steps of inserting a pedicle anchor device body of a pedicle anchor device of the described kind into a vertebra, of pressing a liquefiable element in the longitudinal bore towards the distal side while coupling energy into the liquefiable element, of thereby causing portions of the liquefiable element to be liquefied and pressed out of the at least one hole into bone tissue, and of causing the liquefied portions to re-solidify to provide an additional anchor.

If the pedicle anchor device has an outer shape that is not purely cylindrical but has an outer retention structure, such as a thread, or is helically twisted, the pedicle anchor device is anchored by such a structure. An additional anti-rotation protection possibly required for this anchoring if self-locking is not sufficient may for example be naturally provided by a spine stabilizing rod or similar. Depending on the situation, the surgeon may be free to use a liquefiable element for ensuring an additional anchoring strength—or he may choose to not use liquefiable material if she/he feels that the anchoring strength is sufficient.

In preferred embodiments, the pedicle anchor device is a device according to an embodiment of the first aspect of the invention.

Anchor devices of the above-described kind with a non-circular shaft portion extending from a proximal end and at least one hole from the longitudinal bore outward (and, if necessary, with a head portion proximal of the shaft portion) may also be provided for other applications than as pedicle screws. The shaft of such anchor devices may optionally be helically twisted, for example by 90° as the above-described pedicle anchor device.

Especially, such an anchor device may be used as anchor for the treatment of fractures, especially fractures close to joints where the bone tissue is sometimes comparably weak and where it may difficult to anchor conventional surgical screws.

In order to investigate advantages of the anchoring of a Ti implant using thermoplastic material in comparably weak bone tissue, calculations and experiments were made. Finite Element calculations have been performed for anchors that comprise a Ti core with a rectangular cross section and thermoplastic material that is liquefied by mechanical energy and pressed into structures of surrounding tissue to form, after re-solidification, an anchor. These calculations have revealed—for the example of the anchoring of a pedicle screw—a substantial reduction of the stress. The van Mises strain has been shown to be reduced by between 74.5% for anchors of a circular cross section and 87% for anchors of an H shaped cross section (M. Rollinghoff and S. Saladin, ETH Zurich Master Thesis). This finding was experimentally confirmed by biomechanical experiments on a human Calcaneus. For this, a Schanz screw was compared to a pin-shaped Titanium anchor (core diameter: 4 mm) that was coated by 0.5 mm PLDLA 70/30 and anchored with the aid of mechanical vibrations causing the PLDLA to be at least partly liquefied and pressed into structures of the spongy bone to provide an anchoring therein. The pullout force was measured (over a 2 mm indenter) as a function of the hardness (indentation resistance) of the spongy bone. The pullout force of the coated Ti anchor was significantly superior to the pullout force of the Schanz screw by a factor 2-4, the difference being greater for weak bone tissue.

Also, pullout failure measurements were made using a pedicle screw of the kind depicted in FIGS. 3-5 from cadaveric osteopenic human vertebrae, and for comparison a pedicle screw with a same shape but without thermoplastic material pressed out of radial the holes. The failure force for permanent dislocation was shown to be raised by an average of 124%. A further important finding was a massive improvement of the loosening behaviour of the pedicle screw with thermoplastic material anchoring that was observed as a deviation from the elastic behaviour.

In embodiments that may be embodiments of the first or the second group, the material of the liquefiable element(s) may contain an additional substance, for example for promoting healing or regeneration of for furthering x-ray visibility. For example, the additional substance may be a growth factor, an antibiotic, an inflammation inhibitor or a buffer. More particularly, the additional substance be a drug promoting healing, in particular growth, differentiation and/or regeneration such as a proteinaceous drug like a growth and/or differentiation factor, e.g. of the Bone Morphogenic Protein family (especially BMP 2, 6, 7, for certain applications also BMP 12, 13), an Insulin Growth Factor (e.g. IGF 1), a Platelet Derived Growth Factor (PDGF), a Growth and Differentiation Factor (e.g. GDF 5) etc. and also combinations thereof and/or other an other drug including a non-proteinaceous drug including small molecules (e.g. biphosphonates), possibly in combination with a proteinaceous drug, etc.

In embodiments that may be embodiments of the first or the second group, the liquefiable element(s) may be of a hydraulic cement (such as a polymeric or other hydraulic cement) with thixotropic properties. Such embodiments may be embodiments in which the liquefiable material comprises an additional substance, such as a growth factor. A special example of an anchor device is a device for treatment of a fracture of a neck of a femur where it can replace a state-of-the-art nail that penetrates from the shaft of a femur into its head through the fractured neck, for example in a position and orientation as disclosed in U.S. Pat. No. 3,025,853.

More generally, such an anchor device may be used as stabilizing screw in situations where anchoring in the human or animal bone is difficult and/or where the geometrical restrictions and/or the mechanical load to be borne make a non-circular cross section and for example even twisted shaft advantageous.

In embodiments, the anchor device body comprises a plurality of holes from the longitudinal bore to the outside, and the anchor device comprises a directing structure structured angularly with respect to a longitudinal axis of the longitudinal bore to direct different portions of the liquefiable material to different ones of the holes. 'Structured angularly'—or azimuthally—means that the structure is not constant along the circumference but varies as a function of the azimuthal angle. In this, the directing structure is a structure within the cross section of the longitudinal bore, i.e. if, for example, the longitudinal bore has a circular cross section, the directing structure's radial position is at least partly within the radius of the bore.

The directing structure is then formed by a stop face, against which the distal end of the liquefiable element is pressed during liquefaction. The distal stop face for the liquefiable element may for example close off the longitudinal opening towards the distal side or at least substantially reduce (by for example at least 50%) a distal portion of the longitudinal opening's cross section compared to the proximal portion. An optional, remaining cross section of the longitudinal opening distal portion extending distally from the directing structure may for example serve as a central guiding portion or as distal hole through which liquefied material portions may be pressed out in addition to the holes in wall of the sheath element. The stop face may be formed by the anchor device body. Alternatively, the directing structure is a directing structure of an insert element that is insertable in situ.

In accordance with a further, second aspect of the invention, a method of augmenting hard tissue and/or hard tissue replacement material for insertion of an implant, and an implantation method including such an augmenting method are provided. The implant has an enossal region that after implantation will be anchored in the hard tissue and/or hard tissue replacement material. A profile body as used for the fourth aspect of the invention has a portion the outer profile of which essentially corresponds to the outer profile of at least a part of the implant's enossal region.

Specifically, the implant may have an outer thread, and the profile body then has an outer thread with same thread parameters (such as thread pitch etc.) and same dimension, except that the profile body's extension may optionally be smaller, preferably only to a small extent, than the corresponding extension of the implant. It is also possible that the minor diameter of the thread is essentially identical between the implant and the profile body, whereas the major diameter of the profile body's thread is smaller than the major diameter of the implant's thread.

The profile body further comprises a longitudinal bore reaching distally from a proximal end of the profile body. At least one hole is in the wall surrounding the longitudinal bore. A liquefiable element may be introduced into the longitudinal bore or is present therein. The profile body further comprises a stop face for the liquefiable element against which a distal end of the liquefiable element may be pressed. The profile body is thus a sheath element of the hereinbefore described kind. It may optionally—but not necessarily—be formed according to embodiments of the first aspect of the invention. As the case may be, in addition to the profile body an insert element may be present.

The method according to the second aspect then features the additional steps of:

introducing the profile body into an opening or gap in the hard tissue and/or hard tissue replacement material;

pressing the liquefiable element against the distal stop face while energy impinges on it to cause material of the liquefiable element to be liquefied, to be pressed through the at least one hole, and to be pressed into structures of the bone tissue or other hard tissue or hard tissue replacement material in which the implant will be anchored, to yield a pre-shaped augmented region;

removing the profile body; and inserting the implant so that a contour of the pre-shaped augmented region cooperates with an outer profile of the implant to secure the implant against undesired movements.

Prior to the step of removing the profile body, other steps may be made. For example, the profile body may replace a trial implant, and an x-ray (or other) control of the position and/or other conditions may be made. By this combination the functionalities of the profile body for augmentation and a trial implant, the augmentation process according to the aspect of the invention brings about only few extra steps compared to prior art methods without augmentation.

Generally, the feature that the outer profile of a section of the profile body essentially corresponds to the outer profile of at least a part of the implant's enossal region does not imply that all dimensions in said sections are equal. Rather, the dimensions of the profile body may be different, especially they may be smaller. The feature implies however that the shape of the implant coarsely fits into a space moulded using the profile body in that for each profile feature (i.e. feature that protrudes from a convex basic body such as a cylindrical basic shape) of the implant, there exists a corresponding feature of the profile body, and the profile features of are in an corresponding positional relationship to each other. In the case the implant comprises an outer thread, this implies that the profile body also comprises an outer thread, with a same thread pitch (this does not exclude multiple threads of the implant and accordingly of the profile body). In case the implant comprises a plurality of axial tongues, at defined azimutal angles, the profile body will comprise a corresponding number of axial tongues at same azimuthal angles, etc.

If the profile body is smaller than the implant, the dimensions will preferably vary only slightly. For example, if the implant has a thread, the minor diameter of the thread is for example smaller by at most 5% and is preferably equal. The thread depth of the profile body thread is preferably at least 50% of the thread depth of the implant thread depth.

Often, prior art anchoring of implants such as of bone screws has been confronted with the problem that especially the cancellous bone tissue contributed little to the anchoring stability. This is because cancellous bone tissue may tend to be brittle, and only few trabeculae may contribute to withstanding tearing forces. If the tissue is augmented by, for example, thermoplastic material filling structures within the trabeculae, this problem may at least partly be solved. However, if the thermoplastic material is sufficiently ductile and tough, considerable forces are necessary to screw a self-tapping thread or a separate tapper into the augmented tissue. Often, there is a danger that an augmentation material body comprising the augmentation material and a few trabeculae embedded in the augmentation material breaks loose from the cancellous bone tissue and is rotated as a whole in the tissue.

The approach according to the second aspect of the invention, in contrast, makes possible that even implants with pronounced profile features—such as screws with comparably large thread depths—may be inserted in augmented tissue/material that is comparably very stable and resistive to forces without having to excerpt, during introduction, too high forces.

Embodiments of the method according to the second aspect of the invention may be viewed as moulding an augmented region anchored in the hard tissue and/or hard tissue replacement material to a desired shape for the implant to be introduced in a later step.

A subsequent forming step that includes the removal and/or deformation of material is thus not necessary (though the second aspect of the invention does not exclude an additional forming step). The approach according to the second aspect of the invention may make a gentle but effective augmentation possible.

In embodiments, the profile body is chosen to have between three and five holes in the wall around the longitudinal bore, the holes being at approximately equal axial positions. For example the profile body may be chosen to have exactly four holes in the wall around the longitudinal bore, the holes being at approximately equal axial positions.

In embodiments, the profile body may have an angularly structured directing structure distally of the longitudinal bore to direct different portions of the liquefiable/liquefied material to different ones of the openings.

In embodiments, the profile body has a profile essentially corresponding to at least a section of the enossal portion of a pedicle screw. The method then comprises introducing the profile body, from an essentially dorsal direction, through into the vertebra, and more particularly into the pedicle. The implant implanted subsequently to augmenting is then a pedicle screw.

A kit of parts for carrying out an implantation according to the second aspect of the invention comprises the profile body and the implant (for example pedicle screw). It may further comprise the liquefiable element.

In accordance with a third aspect of the invention, an anchoring device, such as a surgical screw, is provided, the anchoring device comprising an anchoring device body with a longitudinal bore that extends from a proximal end of the anchoring device body and has a hole or a plurality of holes from the longitudinal bore outward, for example radially outward. The anchoring device further comprises a material that can be brought from a flowable state to a non-flowable state, the material for example being thermoplastic or a hydraulic cement with or without thixotropic properties. If the material is a thermoplastic, then the bringing from a flowable to a non-flowable state may merely comprise a letting the previously (fully or partially) melted material cool. If the material is a cement, the bringing from a flowable to a non-flowable state may comprise a hardening the cement. If the material is thixotropic material, the bringing from a flowable to a non-flowable state may comprise a causing the source of the shear stress to stop and to thereby enhance the viscosity.

In accordance with this aspect, the material further comprises an additional substance that may be a drug promoting healing, in particular growth, differentiation and/or regeneration such as a proteinaceous drug like a growth and/or differentiation factor, e.g. of the Bone Morphogenic Protein family (BMP 2, 6, 7; 12, 13)/the transforming growth factor beta family, an Insulin Growth Factor (e.g. IGF 1), a Platelet Derived Growth Factor (PDGF), a Growth and Differentiation Factor (e.g. GDF 5) etc. and also combinations thereof and/or other an other drug including a non-proteinaceous drug including small molecules (e.g. biphosphonates), possibly in combination with a proteinaceous drug, etc.

The anchoring device body is of a material that is not liquefiable under implantation conditions. It may be made of a metal, of a ceramic, of a (potentially reinforced) plastic that does not liquefy under implantation conditions, or of an other suitable biocompatible material. Further, the anchoring device body preferably has an anchoring structure, especially a thread. Especially, the anchoring device body may be a surgical screw, especially a pedicle screw.

The third aspect may be combined with the first aspect (especially the first group of embodiments) of the invention.

The third aspect thus proposes to provide a surgical screw (or similar anchoring device) with a material that comprises a drug promoting healing, which material can be pressed out of the opening(s) from the longitudinal bore outward into the surrounding tissue, especially into cancellous bone tissue. Thus by the method/device in accordance with the third aspect, it becomes readily possible to combine the function of a surgical screw, with brining the healing promoting drug directly into the bone tissue. The material that can be pressed out of the opening(s) has an additional anchoring effect and especially may provide a substantial improvement of the loosening behaviour.

An special class of (matrix) materials in which the additional substance may be embedded is hydraulic cements that are resorbable and/or osteoconductive. A special class of cements is calcium phosphate cements, for example based on $Ca_4(PO_4)_2O$ and $CaHPO_4$ powders mixed with water. Such substances may harden at physiologic conditions. Calcium phosphate cements may harden by ion exchange in the human body; calcium phosphate cements exist that have some stability of a non-hardened phase at room temperature but that harden quickly at body temperature.

Specific examples of suitable Calcium Phosphate Cements are 'ChronOS' and 'Norian' by Synthes.

A further example are not resorbable cements like PMMA cements.

In addition to the drug that promotes healing, the material may comprise a polymer and/or a hydrogel.

If the (matrix) material is a hydraulic cement, mechanical energy, such as mechanical vibrations, may impinge on the material while the material is driven out of the opening(s). Especially, an effect of thixotropy may help to reduce the viscosity so that the driving out of the opening(s) is possible with less force acting on the material from the proximal side.

An other special class of (matrix) materials in which the additional substance may be embedded is resorbable thermoplastic polymers such as the resorbable polymers mentioned hereinafter. Further suitable examples are mixtures of any combination of:
  one or more hydraulic cement(s);
  one or more for example resorbable polymer(s);
  one or more hydrogel(s).

In accordance with the prior art, a damaged bone tissue part is treated by filling a hole or similar by bone cement (that may be provided with growth factors). In contrast thereto, the approach according to the sixth aspect of the invention makes possible a much more targeted treatment wherein the drug, by being pressed out of the opening(s), is applied directly to the interior of the bone tissue, has a more intimate contact therewith, and less or no other tissue than the bone tissue is exposed to the drug.

A further use of bone growth factors (or other additional substance with a clinical effect, especially of the above-described kind) is the following:in a first step, a hydraulic cement comprising a bone growth factor (or other additional substance) is pressed out of the longitudinal bore of a device body of the kind with a longitudinal bore and one or more holes from the bore outward, in a second, subsequent step a thermoplastic element is at least partially liquefied by the impact of mechanical energy, and liquefied portions are pressed out of the hole(s) through which the hydraulic cement had been pressed out.

This sequence of method steps may be used in any aspect of the invention that features using the thermoplastic material for augmenting or anchoring and may be used in any aspect of the invention that features the hydraulic cement as (matrix) material comprising a drug promoting healing. Alternatively, it may be applied independently of the other aspects described herein. It has the following purposes/ effects:
  acceleration of the healing process, improvement of the bone densitiy
  immediate stabilization, prevention of early loosening that would otherwise mechanically prevent osseous consolidation of the implant, e.g. osseointegration.

Since the polymer is quenched and since the heat capacity and heat conductivity of the polymer are much smaller than of the aqueous environment, no thermal damage of the active component in the cement may be expected due to this procedure.

In addition to the above described aspects, the invention features the following additional aspects:
  The use of a body with a longitudinal bore that extends from a proximal end of the body and has a hole or a plurality of holes from the longitudinal bore outward, and mechanical vibrations that by a thixotropc effect reduce the viscosity to administer a hydraulic cement to bone tissue, for example for anchoring, drug delivery, and/or other purposes.
  Liquefaction, by mechanical vibrations, of polymer particles dispensed within a hydraulic cement, for example to influence the viscosity of the heterogeneous mixture, for example for administering the mixture to tissue, for example by pressing it out of a hole a body with a longitudinal bore that extends from a proximal end of the body and has a hole or a plurality of holes from the longitudinal bore outward.
  Liquefaction of a hydraulic cement in combination with a stabilizing polymer phase with a solvent for the polymeric phase and using the replacement of the solvent by water to harden the polymeric phase and thereby the cement. Example: N-Pyrrolidone.
  Using a tube element of a thermoplastic polymer, such as a resorbable PLA, to hold a liquid cement mixture (such as a cement powder dispersed in water), then using mechanical energy (such as mechanical vibrations) to liquefy the thermoplastic polymer, for example in contact with bone tissue, so as to release the cement mixture into surrounding bone tissue, whereafter it may harden.
  In all these aspects, the not liquefiable body (if present) may be a surgical screw with a longitudinal bore, especially a pedicle screw.

All these additional aspects except the last aspect may be combined with the third aspect of the invention and may further be combined with other aspects of the invention. Further, the additional aspects except the last aspect may be combined with each other. The last of the additional aspects may be combined with providing an additional substance in the material, which additional substance may be a drug, such as any one of the above-mentioned drugs.

Embodiments of devices and methods in accordance with all aspects of the invention may be devices/methods for human surgery, or alternatively for (non-human) animal surgery, especially for surgery of dogs, cats or other pets.

In embodiments of the aspects of the invention, the holes through which the liquefied material flows out during implantation/augmentation, may be on a same axial position, or they may be at different axial positions. The angular positions may be evenly distributed around the circumference. In special embodiments, the angular positions may have a deviating distribution adapted for a particular need. For example, if the implant is destined to be an implant for fusing joint parts, and for being inserted in a joint space, the holes (if more than two) may be concentrated on opposed sides to be in contact with the joint areas.

In special embodiments of any aspect of the invention or of any other anchoring or augmentation process that includes pressing liquefied material out of holes in a sheath element, a multi-tiered anchoring or augmentation may be made, with sequentially anchoring/augmenting in different tiers, to each tier being attributed at least one outflow hole (and preferably a plurality of outflow holes). To this end, after anchoring/augmenting on a first tier, an insert element (which may be a first insert element if the sheath element itself comprises a distal stop face or which may be a second insert element if for the anchoring/augmentation at the first tier already an insert element was used) is inserted from the proximal side and caused to stop at a position immediately underneath the second tier. Then, again a liquefaction process is initiated. This may optionally be repeated for a third, or even a fourth, fifth, etc. tier.

In embodiments where the implant does not have a thread, the outer shape of the implant (and/or of the augmentation device) does not need to be generally circularly cylindrical but may have any contour.

Mechanical vibration or oscillation suitable for devices and methods according to embodiments of the invention that include liquefaction of a polymer by friction heat created through the mechanical vibration has preferably a frequency between 2 and 200 kHz (even more preferably between 10 and 100 kHz, or between 20 and 40 kHz) and a vibration energy of 0.2 to 20 W per square millimeter of active surface. The vibrating element (sonotrode) is e.g. designed such that its contact face oscillates predominantly in the direction of the element axis (longitudinal vibration) and with an amplitude of between 1 and 100 µm, preferably around 10 to 30 µm. Rotational or radial oscillation is possible also.

For specific embodiments of devices, it is possible also to use, instead of mechanical vibration, a rotational movement for creating the named friction heat needed for the liquefaction of the anchoring material. Such rotational movement has preferably a speed in the range of 10,000 to 100,000 rpm. A further way for producing the thermal energy for the desired liquefaction comprises coupling electromagnetic radiation into one of the device parts to be implanted and designing one of the device parts to be capable of absorbing the electromagnetic radiation, wherein such absorption preferably takes place within the anchoring material to be liquefied or in the immediate vicinity thereof. Preferably electromagnetic radiation in the visible or infrared frequency range is used, wherein the preferred radiation source is a corresponding laser. Electric heating of one of the device parts may also be possible.

In this text the expression "thermoplastic material being liquefiable e.g. by mechanical vibration" or in short "liquefiable thermoplastic material" or "liquefiable material" is used for describing a material comprising at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 µm and 100 µm, preferably around 10 to 30 µm. Such vibrations are e.g. produced by ultrasonic devices as e.g. known for dental applications. For being able to constitute a load-bearing connection to the tissue, the material at the time of insertion has an elasticity coefficient of more than 0.5 GPa, preferably more than 1 GPa. The elasticity coefficient of at least 0.5 GPa also ensures that the liquefiable material is capable of transmitting the ultrasonic oscillation with such little damping that inner liquefaction and thus destabilization of the liquefiable element does not occur, i.e. liquefaction occurs only where the liquefiable material is at the liquefaction interface to the stop face. The plastification temperature is preferably of up to 200° C., between 200° C. and 300° C. or even more than 300° C. Depending on the application, the liquefiable thermoplastic material may or may not be resorbable.

Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suited thermoplastic material include any one of the polylactide products LR708 (amorphous Poly-L-DL lactide 70/30), L209 or L210S by Böhringer Ingelheim.

Specific embodiments of degradable materials are Polylactides like LR706 PLDLLA 70/30, R208 PLDLA 50/50, L210S, and PLLA 100% L, all of Böhringer Ingelheim. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 Apr;31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate® by DSM, especially Bionate 75D and Bionate 65D; according information is available on datasheets publicly accessible for example via www.matweb.com by Automation Creations, Inc.). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff. (POM—Polyacetal, tradenames Delrin, Tenac, has also been used in endoprostheses by Protec).

The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

If the liquefiable material is to be liquefied not with the aid of vibrational energy but with the aid of electromagnetic radiation, it may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see SM Rea et al., J Mater Sci Mater Med. 2004 September;15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 µm (contents, preferentially 10-25% by volume), sub-micron (nanofillers as from precipitation, preferentially plate like aspect ratio >10, 10-50 nm, contents 0.5 to 5% by volume).

A specific example of a material with which experiments were performed was PLDLA 70/30 comprising 30% (weight percent) biphase Ca phosphate that showed a particularly advantageous liquefaction behaviour.

The material of the sheath element (which may be a screw, especially pedicle screw) may be any material that does not melt at the melting temperatures of the liquefiable material. Especially, the sheath element may be of a metal, for example a titanium alloy. A preferred material is titanium grade5. This material, in addition to being generally suited for implantable devices, has a comparably low heat conduction. Because of this bad heat conduction, the melting zone arising in liquefiable material and at the interface to the directing structure is heated quickly, without the surroundings being heated to too high temperatures. Alternative materials for the sheath element are other metals like other titanium alloys, stainless steel, ceramics like Zirconium oxides or Aluminum oxides, or hard plastics such as PEEK etc.

BRIEF DESCRIPTION OF THE DRAWINGS

In the following, ways to carry out the invention and embodiments are described referring to drawings. The drawings mostly are schematical. In the drawings, same reference numerals refer to same or analogouos elements. The drawings show:

FIGS. 15-17 an embodiment of a sheath element of an implant or augmentation device;

FIG. 18 a detail of a further embodiment of an implant or augmentation device;

FIG. 19 a view of an insert element of the implant or augmentation device of FIG. 18;

DESCRIPTION OF THE PREFERRED EMBODIMENTS

Figure 1:
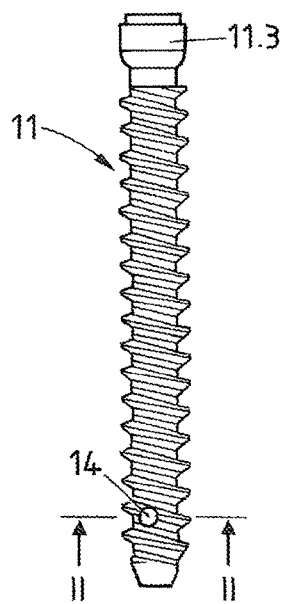
FIGS. 1 and 2 a pedicle screw being an embodiment of a pedicle anchor device.

The device shown in FIG. 1 is a first example of a pedicle screw 11 being a pedicle anchor device body of a pedicle anchor device. The device body 11 is formed as a sheath element with a proximal wall portion 11.1 that surrounds a longitudinal bore 13 open to the proximal side of the sheath element. A distal end portion 11.2 terminates the longitudinal bore distally. A collar portion 11.3 serves as proximal head to which further elements can be fastened.

In the depicted configuration, the distal end portion (meaning that it forms the distal end of the longitudinal bore) is also at the distal end of the pedicle anchor device body; in other embodiments, the device body may comprise a portion distally of the The distal end portion may optionally form a directing structure as illustrated in more detail further below. The wall portion of the sheath element has at least one hole, namely four holes 14 equally distributed around the circumference of the sheath element in the depicted embodiment.

Figure 10:
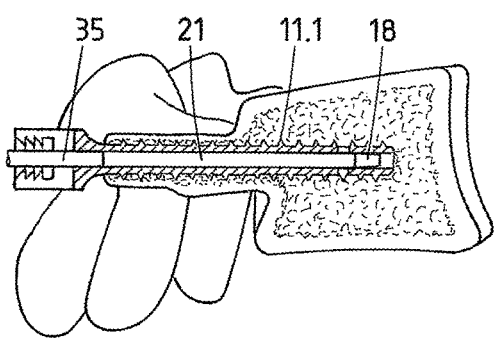

The pedicle anchor device further comprises a liquefiable element 21, for example a polymer pin 21 that is adapted to the sheath element to be inserted in the longitudinal bore 13 from the proximal side, as illustrated for example in FIG. 10.

For the anchoring process, the liquefiable element 21 is inserted and brought into a position where it abuts against the distal end portion. While the sheath element is in contact with hard tissue and/or hard tissue replacement material, the liquefiable element is pressed against the distal end portion while energy impinges from the proximal side. Under the additional effect of the pressing force, the liquefied material of the liquefiable element is pressed out through the holes 14 and into structures, like pores, surface unevenness, inhomogeneities etc. of the hard tissue and/or hard tissue replacement material.

An advantageous way of causing energy to impinge is by way of a sonotrode 35 (see for example FIG. 10) that is pressed against a proximal end face of the liquefiable element while mechanical vibrations are coupled into the sonotrode. The mechanical vibrations are coupled into the liquefiable element 21, and the vibration energy is at least partly absorbed at the interface to the distal end portion causing the polymer material of the liquefiable element to at least locally liquefy at this interface.

Figure 2:
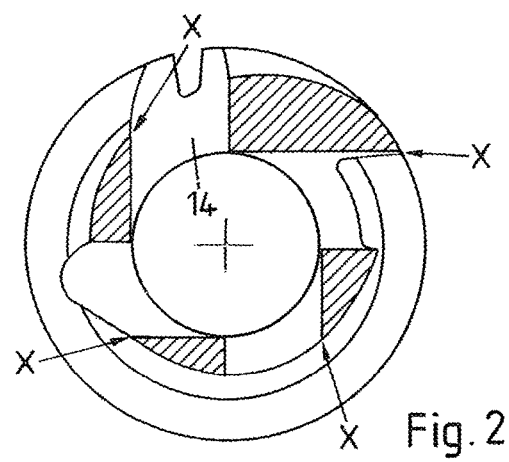

FIG. 2 depicts a section along the plane II-II in FIG. 1 illustrating optional features that may be realized in any embodiment, either alone or in combination.

While most embodiments feature radial holes, the holes 14 of the embodiment of FIGS. 1 and 2 are not strictly radial, but axes of the holes do not go intersect the proximodistal axis. This brings about an asymmetry of the holes with respect to clockwise vs. anticlockwise rotational movements of the device. This in turn produces sharp edges marked by X in FIG. 2. If the device, after the anchoring or augmentation process, is turned in a direction that corresponds to a clockwise rotation in FIG. 2, the liquefied and re-solidified material remaining in the hole is subject to both, a shearing force and a cutting action by the sharp edges X. This will favor a separation between liquefiable material portions outside of the sheath element and interpenetrating the hard tissue and/or hard tissue replacement material on the one hand and liquefiable material portions remaining in the sheath element on the other hand. A configuration where an unscrewing corresponds to a clockwise rotation in FIG. 2 is thus advantageous in cases where the device is an augmentation device, where the sheath element is to be retracted. If, on the other hand, the device after anchoring is turned in a counter-clockwise direction, the force acting on the liquefied and re-solidified material in the holes 14 will have a radial and an axial component, with reduced shearing forces, and no cutting occurs. In such a situation, there will be a strong resistance to a rotational movement. A configuration where an unscrewing corresponds to a counter-clockwise rotation in FIG. 2 is thus advantageous in cases where the device is designed to remain anchored in the body of the patient.

The holes 14 are not at equal axial positions. Rather, the positions may follow the thread. This feature may be advantageous if the sheath element comprises a thread, although an interruption of the thread—if the holes are at equal axial positions or have an other axial position distribution—is in most cases not a problem.

The principle of the outflow holes being asymmetrical with respect to a radial direction may be implemented independent of the first aspect of the invention and possibly independent of any aspect of the invention. It may be used for medical devices comprising a sheath element suitable of being brought into contact, during a surgical operation, with live hard tissue and/or with hard tissue replacement material, which is based on the liquefiable material being inserted (pre-assembled or inserted in situ) in a longitudinal bore of the sheath element and where the sheath element comprises at least one hole in the sheath element wall, through which the liquefied material is pressed from the longitudinal bore into the structures (pores or cavities or other structures) of the bone tissue or other hard tissue or hard tissue replacement material in which anchoring is desired.

The possibility to remove an implant after implantation is a requirement of most surgical operations. If the above-described approach of shearing off polymer material that has flown out of the sheath element (with or without the asymmetric configuration of FIG. 2) is not possible or not sufficient, other approaches may be used, either alone or in combination with each other and/or in combination with shearing off:

- removing liquefiable material by drilling into the longitudinal bore and subsequent pulling or rotating
- heating liquefiable (thermoplastic) material to a temperature at which it is again liquid or at least less stiff.

Figure 3:
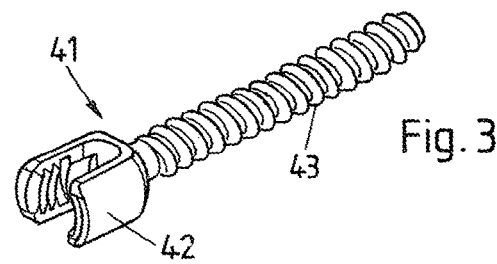
FIGS. 3-5 a further pedicle screw being an embodiment of a pedicle anchor device.
Figure 4:
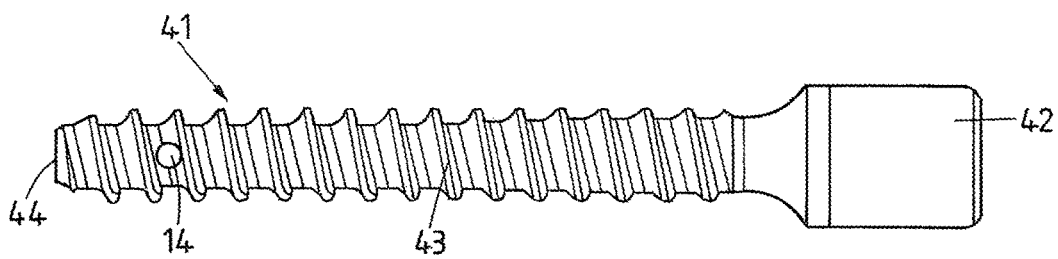
Figure 5:
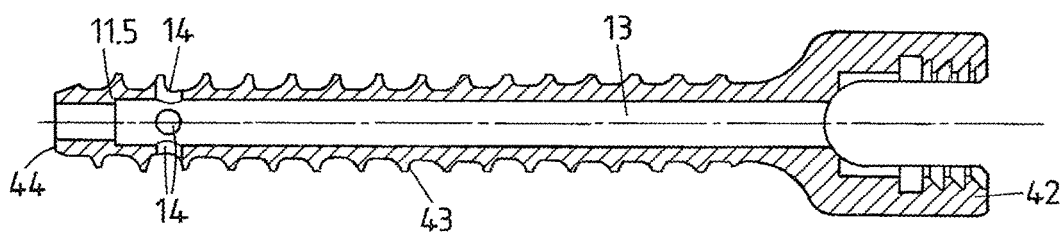

Referring to FIGS. 3, 4, and 5, a bone screw, namely a further pedicle screw 41 is depicted. The pedicle screw is, together with a thermoplastic element not shown in FIGS. 3-5, an embodiment of a pedicle anchor device according to the first aspect of the invention. Further, a pedicle screw of the kind depicted in FIGS. 3-5 may be an embodiment of an anchoring device body of an anchoring device according to the third aspect.

The pedicle screw 41 comprises a screw head 42, a threaded section 43, and a distal end portion 44. The pedicle screw further comprises a longitudinal through bore 13 that, towards the distal end, comprises a narrowed portion so that a shoulder 11.5 for stopping an insert element (not shown in FIG. 5) acting, during the liquefaction, as the distal end of the longitudinal bore 13 and inserted from the proximal side is formed.

The thread has a constant outer diameter (major diameter), whereas a core diameter (minor diameter) is larger at the proximal side than at the distal side. More concretely, in the depicted embodiment, in a central portion of the threaded section the core diameter gradually reduces, whereas in peripheral portions the core diameter is constant. In other, alternative embodiments, the core diameter is constant, is gradually reduced along the entire length of the threaded section, or the core diameter has a stepped characteristics as taught in WO 90/02526, or has any other characteristics. Also, the outer diameter of the threaded section need not be constant. Generally, the approach according to the first aspect of the invention may be combined with any suitable outer thread. Compared to prior art pedicle screws with a longitudinal bore, the bore diameter is comparably large to make insertion of the liquefiable element—that may be a polymer pin—possible. In the depicted embodiment, the bore diameter at the more proximal portion of the threaded section is 3.1 mm and at the distal portion of the threaded section is 2.9 mm, whereas the major diameter is 6.6 mm and the minor diameter is between 4.4 mm and 5.3 mm. The resulting wall strength has proven to be sufficient.

The screw head is flattened and comprises an inner thread that can be used for coupling to an apparatus for automated implantation, as described in U.S. patent application No. 61/259,383 incorporated herein by reference.

Figure 6:
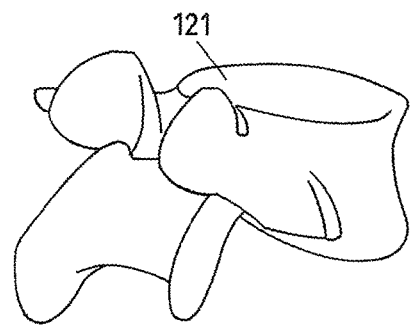
FIGS. 6-12 steps of a method of implanting a pedicle screw as depicted in FIGS. 3-5.
Figure 7:
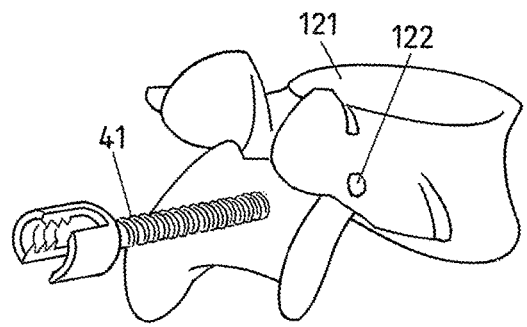
Figure 8:
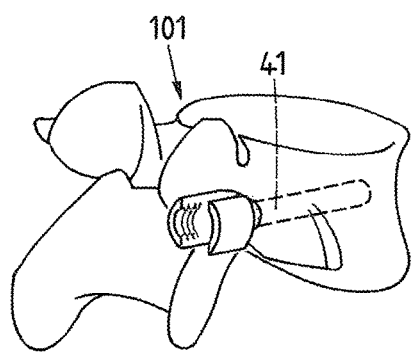
Figure 9:
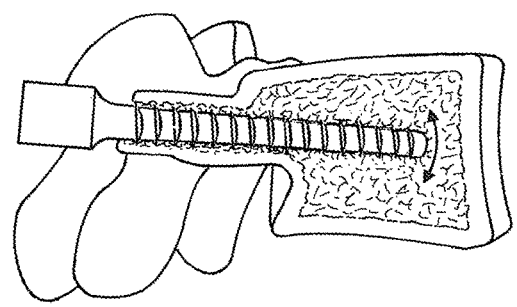
Figure 11:
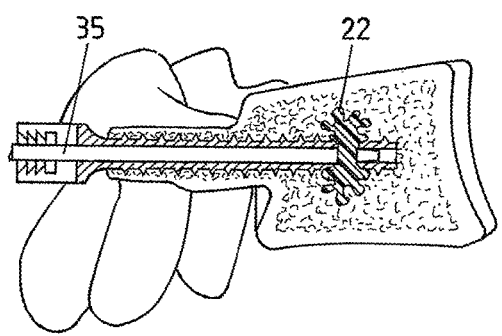
Figure 12:
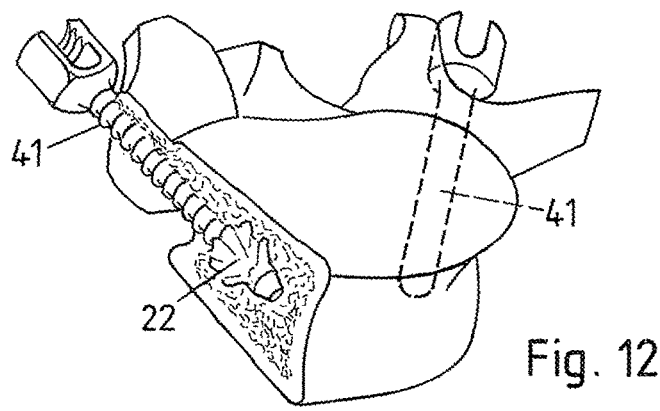

Referring to FIGS. 6-12 yet a process of anchoring a pedicle screw of the kind illustrated in FIGS. 3-5 is illustrated. FIG. 6 depicts a vertebra 121. As shown in FIG. 7, in a first step, the access is prepared by pre-drilling a bore 122 at the appropriate position in a region near the transverse process. The bore 122 may merely go through the cortical bone, or it may reach through the pedicle into the vertebral body and over an entire length of the pedicle screw to be introduced later, or a substantial portion thereof. In order to enhance the bone density, the pre-drilled hole may be drilled to have an undersize. After the preparation of the bore 122, the pedicle screw 41 is inserted conventionally by screwing. (FIG. 8, FIG. 9). The orientational stability, due to the limited strength of the cancellous bone in the vertebral body, may be limited as illustrated by the double arrow in FIG. 9. Thereafter, the liquefiable element 21 being a pin of a thermoplastic polymer is inserted. If the screw is of the type having a separate insert element for the directing structure, prior to or together with the liquefiable element 21 also the insert element 18 is inserted. Then, as shown in FIG. 10, the sonotrode 35 acts to press the liquefiable element against the stop face while coupling mechanical vibrations into the liquefiable element. The resulting liquefaction, followed by a re-solidification is illustrated in FIG. 11. FIG. 11 illustrates the situation during the anchoring process. Liquefied and re-solidifying material portions 22 pressed into the surrounding bone tissue of the vertebra and interpenetrating structures of the latter strengthen the cancellous bone tissue. In addition, together with portions of the liquefiable material that remain, after re-solidifying, in the device body, the connection provides a solid anchoring. FIG. 12 illustrates, in partial section, the two pedicle screws 41 inserted by this method.

Figure 13:
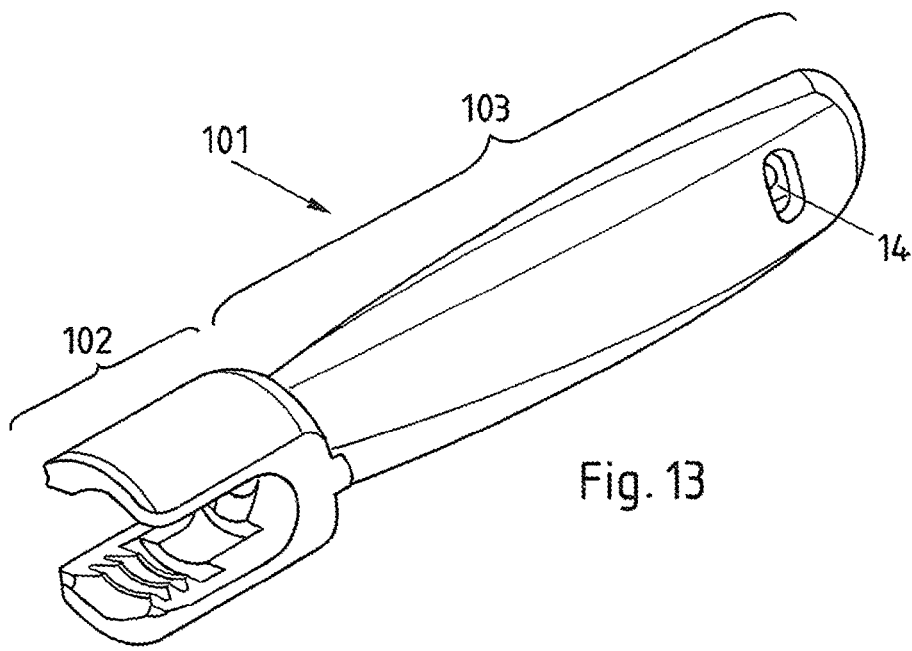
FIG. 13 an other embodiment of a pedicle anchor device.
Figure 14:
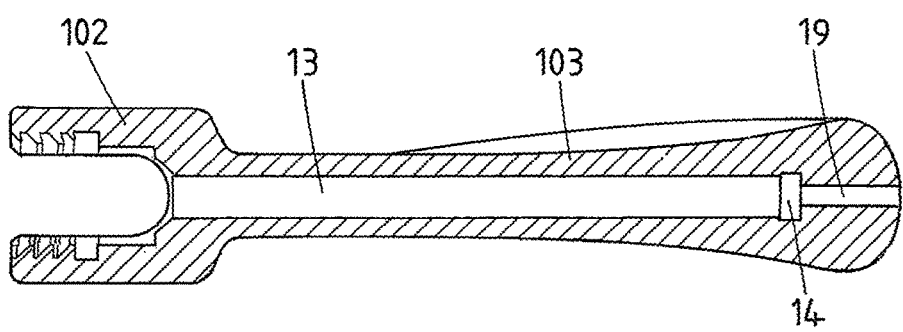
FIG. 14 a section through the embodiment of FIG. 13.

The pedicle anchor device 101 shown in FIGS. 13 and 14 is a further example of a device according to the first aspect of the invention. In particular, it is an embodiment of a device according to the second group of embodiments. The head portion 102 is similar to the head portion of the pedicle screw described referring to FIGS. 3- 5. Its inner thread may not only be used for coupling to an apparatus for automated implantation but also for the fixation of a spine stabilizing rod.

Instead of the depicted head portion, other head geometries of existing or new spine stabilizing configurations may be used.

The shaft portion 103 does not have a circular cross section (such as for example a shape that corresponds essentially to a circular cylinder or to a cone) and does therefore not have an outer thread. Rather, the shaft portion is flat and is helically twisted. In the depicted configuration, the total angular twist amounts to about 90°, so that a distal end portion of the shaft is approximately perpendicular to a proximal portion intended to be located in the pedicle after implantation. By this, the pedicle anchor device may have a 'vertical' orientation at the proximal end, an inclined orientation following the direction of longest extension of the pedicle cross section within the pedicle and a 'horizontal' orientation within the vertebral body.

The pedicle anchor device comprises a longitudinal bore 13 for a thermoplastic element (not shown) to be inserted. Two radial holes 14 reach from the longitudinal bore to an outside. They are arranged near to the distal end of the shaft portion at the two flat sides. Like in the previously described embodiments, a thermoplastic element is inserted in the longitudinal bore and then for anchoring mechanical energy is coupled into the thermoplastic element to liquefy portions thereof and to press the liquefied portions out of the radial holes into structures of the surrounding tissue.

In the depicted embodiment, the pedicle anchor device—like other embodiments—has an additional distal (axial) hole 19 that may for example serve as guiding hole together with a Kirschner wire and/or may serve for pressing out further portions of liquefied material into tissue at the distal end of the device. Such an additional distal (axial) hole may especially be advantageous in embodiments, in which like in the embodiment of FIGS. 13 and 14 the distal end portion of the longitudinal bore against which the liquefiable material is pressed during liquefaction is not formed by a separate insert but by the device body itself.

A device of the kind shown in FIGS. 13 and 14 may further optionally comprise a directing structure that is structured angularly with respect to a longitudinal axis of the longitudinal bore to direct different portions of liquefiable material from a liquefiable element to different ones of the holes 14, as described hereinafter.

Figure 24:
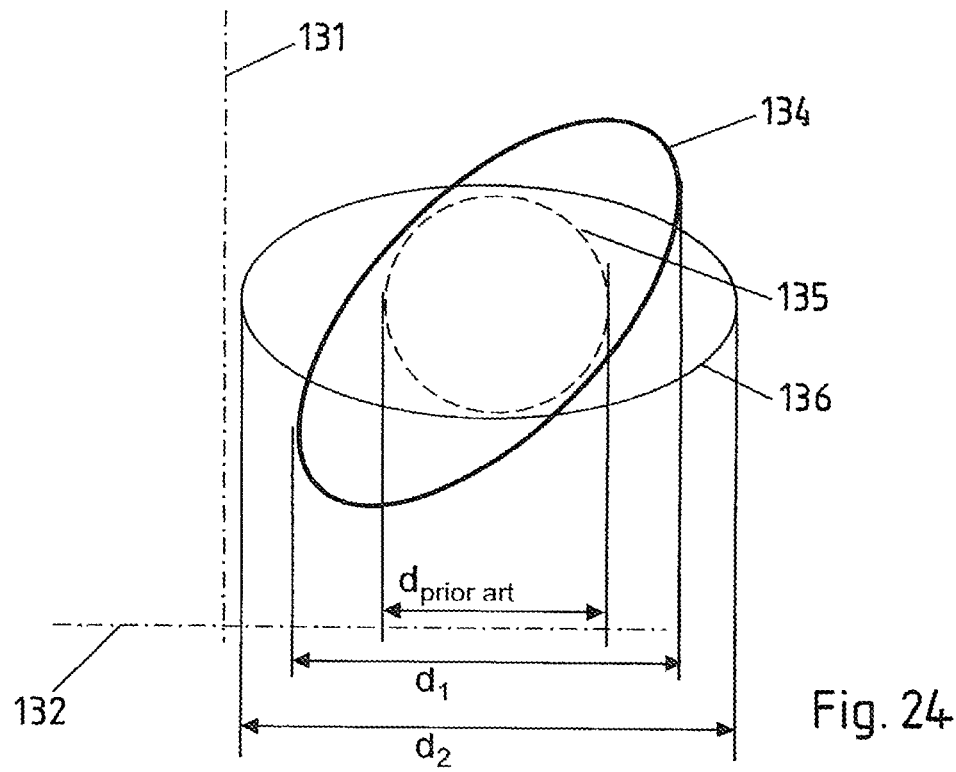
FIGS. 24 an illustration showing the effects of a pedicle anchor device that does not have a circular cross section and of a pedicle anchor device with a twist, and FIG. 25 a further embodiment of a pedicle anchor device and method.

The effects of the flat, not circular cross section and of the twist are schematically illustrated referring to FIG. 24. In FIG. 24, the extension of bone tissue within the pedicle in which an pedicle anchor device may be anchored is schematically shown by the ellipse 134. The axes 131, 132 are parallel to the sagittal plane and the transversal plane, respectively. Prior art pedicle anchor devices are restricted to a circular cross section. The maximal possible cross section thus corresponds to the dashed line 135 in FIG. 24. This sets an upper limit of the effective anchoring cross section $d_{prior\ art}$. A pedicle anchor device according to aspects of the invention does not need to be circular, due to the new anchoring technique with liquefiable material pressed out of the longitudinal bore. Thus, the entire available cross section of the pedicle may be used if an anchoring device with a for example elliptical cross section is used, leading to an enhanced effective anchoring cross section $d_1$. By a twist as for example in the embodiments of FIGS. 13 and 14, the orientation of the more distal implant sections may be different from the orientation within the pedicle, leading to an even more enhanced effective anchoring cross section $d_2$. This brings an improved anchoring strength.

If the quality of the bone tissue of the patient does not require such an enhanced effective anchoring cross section, then a pedicle anchor device with a reduced cross section may be used, so that the overall cross sectional area is smaller than the cross sectional area of prior art pedicle screws (as illustrated by the dashed line), so that the implantation causes less impact on the tissue.

Figure 25:
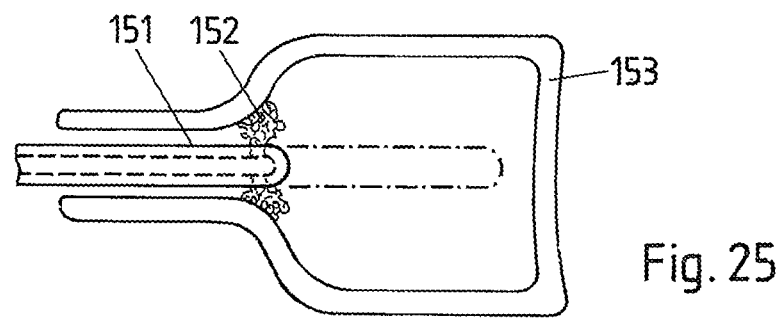

A further embodiment of a pedicle anchor device and of an according method is very schematically illustrated in FIG. 25. FIG. 25 shows a cross section through a portion of a vertebra along the vertical plane parallel to the pedicle anchoring device insertion axis. In contrast to the prior art pedicle screws and to the embodiments described hereinbefore, the pedicle anchoring device's 151 length is adapted to the size of the patient's vertebra so that the anchoring device ends where the pedicle adjoins the vertebral body. This has the following advantages:

compared to prior art pedicle screws, (the approximate extension of which is sketched by the dotted line in FIG. 25), less bone tissue is affected by the insertion of the device the material 152 flown out through the holes is at a position where the bone quality is often better. Also, the cortical bone 153 may cause an additional stability in that the material 152 may find direct mechanical support by the cortical bone 153. Also a kind of rivet effect may be achieved in that the material occupies a region around the implant that is larger in cross section than the region encompassed by the cortical bone immediately proximally of the material 152.

The latter effect may also be used in case the pedicle anchor device extends further into the vertebral body but the position of the holes to which the material flows out corresponds to the one of the device of FIG. 25.

Whereas in the illustrated embodiments, the head portion and the shaft portion are illustrated to be one-piece, this is not necessary. Rather, they may be separate pieces somehow attached to each other. Especially, the connection between the shaft portion and the head may be so that the orientation of the head portion relative to the shaft portion may be adjustable. The head portion may be rotatable about an axis, or the adjustability may be multi-axial.

The hereinbefore described embodiments may, in addition or as an alternative to the mentioned optional features, be provided in the following variants:

Multi-tiered anchoring or augmentation with a plurality of insert elements sequentially inserted, the second, more proximal insert element inserted after anchoring or augmentation with the first, more distal insert element, or with a distal directing structure of the sheath element and with at least one insert element to be placed proximally of the distal directing structure after anchoring with the latter. In this, the sheath element comprises one or more holes for each of the different insert elements or for the distal directing structure and the at least one insert element. The sheath element may comprise a plurality if inner shoulders so have a stepwise reduced cross section towards the distal side, or may comprise different guiding grooves reaching to different distal positions for the different insert elements.

The number of holes 14 attributed to a particular directing structure does not need to be four as in the illustrated embodiments but may be two (like in FIGS. 13 and 14), three, five, six, etc. Also, the angular (azimuthal) spacing does not need to be equal between all holes but may be adapted to a particular situation. For example, for introduction of an implant in a gap of a joint, the sheath element may comprise two pairs of neighboring, relatively close holes at opposite sides. In the case of multi-tiered anchoring, each tear may have an individual number and distribution of holes.

The holes may have different shapes and/or different sizes.

The multi-tiered anchoring or augmentation as described herein with a first liquefaction process taking place with a first directing structure—of the sheath element or of an initially separate insert element—the subsequent (after an at least partial re-solidification of the liquefied material) addition of a further directing structure of a (second) insert element and then a second liquefaction may be applied independent of the aspects of the invention.

In FIGS. 15-19 yet further embodiments of the anchoring device or details thereof are illustrated. These further embodiments/details comprise a directing structure that is structured angularly with respect to a longitudinal axis of the longitudinal bore to direct different portions of the liquefiable material to different ones of the holes.

FIGS. 15-17 show a first such embodiment. The directing structure comprises a ramp portion 12 sloping away from a center around the longitudinal axis. The ramp portion 12 is conical, thus its section with a plane going through the longitudinal axis is a straight line. In alternative embodiments, it could be spherical and concave. At the radially outer side of the ramp portion, the wall portion of the sheath element has four holes 14 equally distributed around the circumference of the sheath element. At angular positions between the holes, the directing structure further comprises walls 15 angularly sub-dividing a portion of the longitudinal bore volume communicating with the holes 14. In the depicted embodiment, the walls have a constant thickness and comprise a proximal edge 15.1 that in the depicted embodiment slope towards the center The angular structuring of the directing structure with the walls between the holes firstly has the function to separate portions of the liquefiable element during liquefaction. Due to this, approximately equal amounts of liquefied material is pressed out of every one of the four holes 14, even if the liquefied material while being pressed out of the different holes 14 encounters different resistance. A second function of the walls 15 that protrude distally from the directing structure body and the stop face is that of energy directors. The liquefiable material will have a tendency to start liquefying, under the impact of mechanical vibrations, at edges or other pronounced structures either of the sheath element or of the liquefiable element itself. The energy directing function of the walls 15 is a means for causing the liquefaction to start and take place in vicinity of the holes 14 and not, for example, at the proximal interface to the sonotrode where too early an onset of liquefaction would be undesired.

FIGS. 18 and 19 show a detail of a pedicle anchor device, for example as illustrated in FIGS. 3-5. Compared to the embodiment of FIGS. 15-17, the embodiment of FIGS. 18 and 19 incorporates the following features:

- The outer side of the sheath element comprises an outer thread 11.4.
- The longitudinal bore 13 is a through bore, making the device suitable for being guided by a wire in minimally invasive surgery. The through bore is narrowed towards the distal side so that a shoulder 11.5 is built. The shoulder serves as a stop structure for an insert element 18 that terminates the longitudinal opening for the liquefiable element towards the distal side and that comprises the directing structure including the walls 15 and the ramp portions 12. The insert element comprises a distal tapered portion 19 that together with the shoulder 11.5 co-operates to form a force fit.
- The walls 15 protrude proximally further than the holes 14. By this, the effect of a controlled distribution of liquefied material between the different holes is effective even if the resistance encountered for liquefied material pressed out of the holes differs strongly between the holes because the interface between liquefied material and still solid material may be expected to be proximal of the upper (most proximal) end of the holes 14.

Other stop structures would be possible. For example the sheath element may comprise at least one interior axial groove that reaches from the proximal end of the sheath element to a distal stop and in which a corresponding number of ridges or tongues of the insert element is guided. Such an embodiment features the additional advantage that the angular relative orientation of the sheath element and the insert element is well-defined during insertion. As an even further variant of a stop structure, the insert element may comprise a spring deflected, during insertion in the sheath element, radially inward against a spring force and forcing a stop flange portion into an annular stop groove of the sheath element at the appropriate axial position. Various other stop structures are possible.

In different embodiments, an insert element 18 may comprise an isotropic stop face instead of an angularly structured stop face.

In further variants, a different number of holes may be present, for example one, two, three, five, . . . holes. The directing structure, if any, is shaped accordingly. The holes may have any appropriate shape, such as circular, elongate, . . .

All of these features may be present alone, in combination or in any sub-combination Referring to FIGS. 20-23, a method for augmenting hard tissue and/or hard tissue replacement material and for implanting a bone screw is described.

Figure 20:
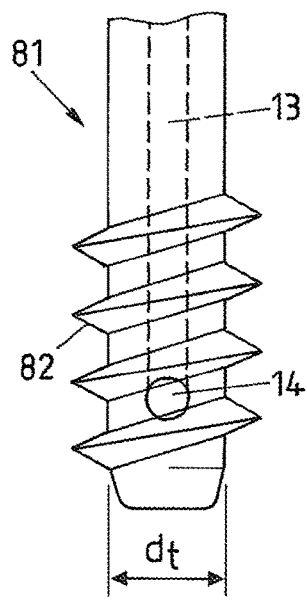
FIG. 20 a profile body for a process according to the fourth aspect of the invention.

The augmentation device comprises a profile body 81 as illustrated in FIG. 20. The profile body is a sheath element with a longitudinal bore 13 and a plurality of holes 14. The profile body further comprises a portion (that may correspond to the entire body or a part thereof) in which the outer profile essentially corresponds to the profile of an implant to be implanted in a later step. Especially, the profile is the profile of a shaft of a bone screw. To this end, the profile body 81 comprises an outer thread 82. The dimensions of the profile body—the drawing illustrates the profile body minor diameter $d_r$—correspond to the dimensions of the implant or are slightly less than the dimensions of the implant. FIG. 20 shows the minor diameter $d_s$ of the thread of the screw. Features relating to relative quantities like the thread pitch are identical between the profile body and the implant.

The augmentation device may be a device comprising an angularly structured directing structure to direct different portions of the liqufiable material to different ones of the holes 14. Alternatively, the profile body may be a sheath element in which a directing structure, against which the liquefiable material is pressed, is not angularly structured.

The profile body's outer thread may be a self-tapping thread. Alternatively, a thread may be added by a different means, such as a separate tapper.

Figure 21:
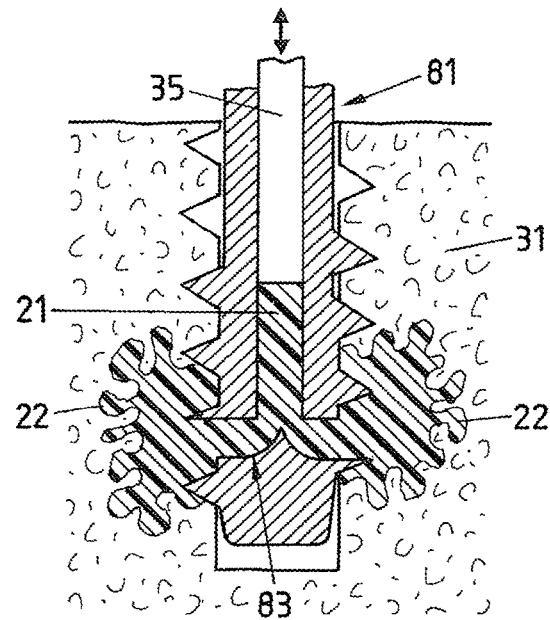
FIG. 21 the profile body of FIG. 20 during the augmentation process.

In a first step, illustrated by FIG. 21, the profile body 81 is inserted in a pre-drilled bore in the hard tissue and/or hard tissue replacement material or in an other opening or gap in the hard tissue and/or hard tissue replacement material, such as a joint space. A liquefiable element that is at least partly liquefiable by the impact of energy is placed, before or after insertion of the profile body, in the longitudinal bore 13. A sonotrode 35 presses the liquefiable element against a directing structure 83 of the sheath element while mechanical vibrations are coupled into the liquefiable element by the sonotrode. This causes material to liquefy and to be pressed through the holes 14 into structures of the hard tissue and/or hard tissue replacement material 31.

After all liquefiable material or a sufficient quantity thereof is liquefied, the mechanical vibrations are stopped, and the sonotrode is retracted. The profile body 81 having the outer thread is removed by a twisting movement. In a variant, it is possible to remove the profile body and the sonotrode together by the twisting movement.

Whereas FIG. 21 illustrates the profile body with a longidudinal bore that is distally closed off by the directing structure 83. In alternative configurations, it is also possible to provide an additional, distal, approximately axial hole. By appropriately choosing the length and diameter of the hole, the amount of liquefied material pressed out through such axial hole (if any) compared to the amount of liquefied material pressed out throught the other, radial holes may be engineered. As a general rule, the higher the ratio between the diameter and the depth of the hole, the larger the amount of material exiting. If the ratio is kept below a certain limit, no material will exit through the axial hole, but the material will 'freeze' in the hole.

Figure 22:
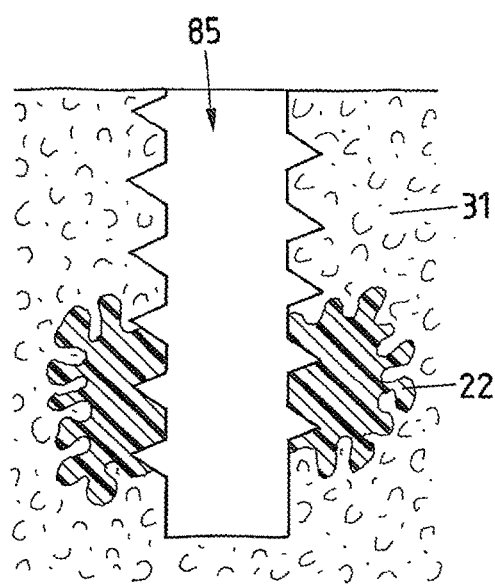
FIG. 22 the resulting augmented tissue with a molded augmented region.
Figure 23:
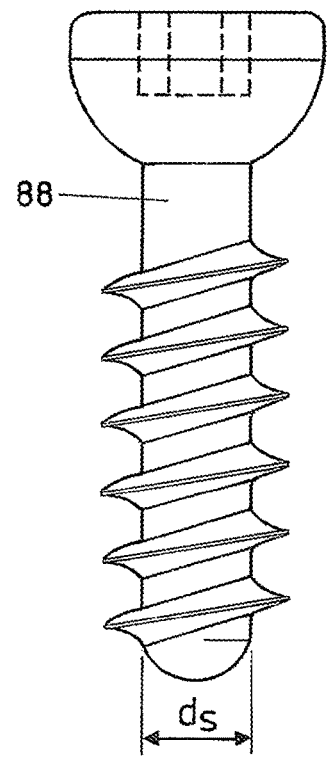
FIG. 23 an implant to be implanted after augmentation.

FIG. 22 illustrates the hard tissue and/or hard tissue replacement material in section after the augmentation process. The opening 85 in the hard tissue and/or hard tissue replacement material comprises the thread, and the wall of the opening is at least in regions fortified by the liquefied and re-solidified material 22 that serves as augmentation material. Especially when the hard tissue and/or hard tissue replacement material has a low density and/or tends to be brittle, this fortification brings about a major improvement in the strength of the anchoring of the bone screw 88 (FIG. 20) inserted thereafter.

The bone screw may be a bone screw based on anchoring according to the state of the art, namely based on anchoring by the thread and by friction forces. The augmentation process brings about an improved anchoring of such a bone screw both, in terms of resistance against pulling forces and in stability of the orientation.

Alternatively, the bone screw may itself comprise a longitudinal bore and holes in the wall for pressing out liquefiable material. Such liquefiable material may be pressed out at positions where the hard tissue and/or hard tissue replacement material is fortified by liquefiable material, so that a welding process between the augmentation material and the newly introduced liquefiable material may take place. In addition or as an alternative, the liquefiable material may be pressed out at positions where the hard tissue and/or hard tissue replacement material is not fortified the augmentation material, so that an additional anchoring may result.

This process is independent of the common shape of the implant and the profile body. Especially, any kind of thread may be used, and the diameter may be constant or not. Also, shapes with features different from a thread may be used, such as cylindrical or not-cylindrical shape with longitudinal ridges and/or indentations, implants with shapes adapted to the body part in which they are implanted (for example joint implants), etc. In all embodiments of this aspect, the profile body may be used as a trial implant.

What is claimed is:

1. A kit of parts for being used in a method of anchoring an implant in hard tissue and/or hard tissue replacement material, the kit comprising:
    an implant, said implant having an enossal region with an enossal region shape, and
    a profile body for being used for an augmentation step in a method of anchoring the implant, in hard tissue and/or hard tissue replacement material, the profile body comprising an outer shape and a longitudinal bore reaching from a proximal end into a distal direction, and a plurality of holes in a lateral wall around the longitudinal bore,
    wherein an outer shape section of the outer shape of the profile body corresponds to the enossal region shape so that a contour of a pre-shaped augmented region cooperates with an outer shape of the enossal region shape of the implant,
    wherein the profile body further comprising a distal stop face terminating the longitudinal bore distally, whereby a liquefiable element is pressable against the distal stop face while energy impinges on the liquefiable element to cause material of the liquefiable element to be liquefied, to be pressed through the plurality of holes and to be pressed into structures of the hard tissue or hard tissue replacement material in which the implant will be anchored, to yield a pre-shaped augmented region, and wherein the distal stop face forms an angularly structured directing structure that is disposed within a cross section of the longitudinal bore to direct different portions of the liquefiable/liquefied material to different ones of the plurality of holes.

2. The kit of parts according to claim 1, wherein the implant has an implant outer thread with an implant thread pitch and the profile body has a profile body outer thread with a profile body thread pitch, the profile body thread pitch being identical with the implant thread pitch.

3. The kit of parts according to claim 2, wherein a minor diameter of the thread or the profile body is equal to a minor diameter of the thread of the implant or is smaller by at most 5%.

4. The kit of parts according to claim 2, wherein a thread depth of the profile body thread is at least 50% of a thread depth of the implant thread depth.

5. The kit of parts according to claim 1, wherein the profile body has between three and five holes in the lateral wall around the longitudinal bore, the holes being at approximately equal axial positions.

6. The kit of parts according to claim 1, wherein the longitudinal bore is distally closed off by the stop face.

7. The kit of parts according to claim 1, comprising a distal approximately axial hole through the distal stop face.

8. The kit of part according to claim 1, wherein the implant and the profile body have a cylindrical or not-cylindrical shape with longitudinal ridges and/or indentations.

9. The kit of parts according to claim 1, and comprising a liquefiable element, at least a portion of which is arranged in the longitudinal bore or fits into the longitudinal bore.

10. A method of anchoring an implant in hard tissue and/or hard tissue replacement material, the method comprising the steps of:
    providing a kit of parts, the kit comprising:
    the implant, said implant having an enossal region with an enossal region shape; and
    a profile body for being used for an augmentation step in the method of anchoring the implant, in hard tissue and/or hard tissue replacement material, the profile body comprising an outer shape and a longitudinal bore reaching from a proximal end into a distal direction, a distal stop face terminating the longitudinal bore distally, and a plurality of holes in a lateral wall around the longitudinal bore, whereby the distal stop face forms an angularly structured directing structure that is disposed within a cross section of the longitudinal bore;
    wherein an outer shape section of the outer shape of the profile body corresponds to the enossal region shape so that a contour of a pre-shaped augmented region cooperates with an outer shape of the enossal region shape of the implant, providing an initial opening in the hard tissue and/or hard tissue replacement material;

pressing a liqefiable element against the distal stop face while energy impinges on the liquefiable element to cause material of the liquefiable element to be liquefied, pressed through the plurality of holes, and pressed into structures of the hard tissue or hard tissue replacement material in which the implant will be anchored, to yield a pre-shaped augmented region, and wherein the distal stop face directs different portions of the liquefiable/liquefied material to different ones of the plurality of holes, allowing the liquefied material to harden and to thereby become augmentation material;

removing the profile body; and anchoring the implant in the opening so that a contour of the pre-shaped augmented region cooperates with an outer shape of the implant to secure the implant against undesired movements.

11. The method according to claim 10, wherein the enossal region of the implant comprises an outer thread having an implant thread pitch, and wherein the profile body is chosen to comprise an outer thread with a profile body thread pitch corresponding to the implant thread pitch.

12. The method according to claim 10, wherein the dimensions of the outer shape section of the profile body are identical to or smaller than the corresponding dimensions of the section of the enossal region profile of the implant.

13. A kit of parts for being used in a method of anchoring an implant in hard tissue and/or hard tissue replacement material, the kit comprising:

an implant, said implant having an enossal region with an enossal region shape, a profile body for being used for an augmentation step in a method of anchoring the implant in hard tissue and/or hard tissue replacement material, the profile body comprising an outer shape and a longitudinal bore reaching from a proximal end into a distal direction, and a plurality of holes in a lateral wall around the longitudinal bore, and an insert element that is insertable in situ, wherein an outer shape section of the outer shape of the profile body corresponds to the enossal region shape so that a contour of a pre-shaped augmented region cooperates with an outer shape of the enossal region shape of the implant, wherein the insert element further comprises a distal stop face terminating the longitudinal bore distally, whereby a liquefiable element is pressable against the distal stop face while energy impinges on the liquefiable element to cause material of the liquefiable element to be liquefied, to be pressed through the plurality of holes and to be pressed into structures of the hard tissue or hard tissue replacement material in which the implant will be anchored, to yield a pre-shaped augmented region, and wherein the distal stop face forms an angularly structured directing structure that is disposed within a cross section of the longitudinal bore to direct different portions of the liquefiable/liquefied material to different ones of the plurality of holes.

* * * * *